US009119576B2

(12) United States Patent
Utagawa

(10) Patent No.: US 9,119,576 B2
(45) Date of Patent: Sep. 1, 2015

(54) OPHTHALMIC DEVICE

(71) Applicant: CANON KABUSHIKI KAISHA, Tokyo (JP)

(72) Inventor: Tsutomu Utagawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/595,041

(22) Filed: Jan. 12, 2015

(65) Prior Publication Data

US 2015/0124217 A1    May 7, 2015

Related U.S. Application Data

(63) Continuation of application No. 13/904,783, filed on May 29, 2013, now Pat. No. 9,022,566.

(30) Foreign Application Priority Data

Jun. 1, 2012  (JP) .................................. 2012-126190

(51) Int. Cl.
| A61B 3/14 | (2006.01) |
| A61B 3/00 | (2006.01) |
| A61B 3/10 | (2006.01) |
| A61B 3/12 | (2006.01) |

(52) U.S. Cl.
CPC ................. *A61B 3/14* (2013.01); *A61B 3/0041* (2013.01); *A61B 3/1015* (2013.01); *A61B 3/1025* (2013.01); *A61B 3/12* (2013.01)

(58) Field of Classification Search
USPC .................................................. 351/200–246
See application file for complete search history.

(56) References Cited

FOREIGN PATENT DOCUMENTS

| JP | 2002-200043 A | 7/2002 |
| JP | 2003-126042 A | 5/2003 |
| JP | 2004-033275 A | 2/2004 |

*Primary Examiner* — Mohammed Hasan
(74) *Attorney, Agent, or Firm* — Canon U.S.A., Inc. IP Division

(57) ABSTRACT

There is provided an ophthalmic device that includes a plurality of light sources including at least a light source for obtaining a return light of which aberration has been corrected with a correction unit from an eye under examination; and a control unit configured to control measurement lights from the plurality of light sources such that the measurement lights enter the eye under examination in a predetermined order when a photography of a second eye is started after a photography of a first eye has been completed.

10 Claims, 8 Drawing Sheets

OPHTHALMIC DEVICE

CROSS-REFERENCE TO RELATED APPLICATIONS

This application is a continuation of U.S. patent application Ser. No. 13/904,783 filed May 29, 2013 Now U.S. Pat. No. 9,022,566 B2, which claims the benefit of Japanese Patent Application No. 2012-126190, filed Jun. 1, 2012, all of which are hereby incorporated by reference herein in their entirety.

BACKGROUND OF THE INVENTION

1. Field of the Invention

The present invention relates to an ophthalmic device.

2. Description of the Related Art

A Scanning Laser Ophthalmoscope (SLO) that is an ophthalmic device using the principle of a confocal laser microscope scans, for example, the eye fundus of an eye under examination with a laser that is a measurement light and performs a raster scan or the like in order to rapidly obtain a high resolution planar image according to the intensity of the return light from the eye under examination. Discussions for the practical use of the device are ongoing in these days. Hereinafter, such a device configured to take a planar image is sometimes referred to as an SLO device.

Further, a technique for measuring an aberration of an eye under examination with a wave-front sensor in real time and correcting the aberration generating at the eye under examination with a wave-front correction device is known. An Adaptive Optics SLO device (hereinafter, sometimes referred to as an AOSLO device) that includes an adaptive optical system for correcting such an aberration with a wave-front correction device has been developed and thus a high lateral resolution planar image can be obtained (Japanese Patent Application Laid-Open No. 2010-259543). Further, Japanese Patent Application Laid-Open No. 2010-259543 discloses that a planar image of a fundus image with a wide angle of view can be obtained. An image is usually taken while the aberration is corrected with a wave-front correction device after the imaged region has been checked using the planar image of the fundus image with a wide angle of view. Thus, after one eye has been imaged, the photography may be performed at a state in which an aberration has been corrected with the wave-front correction device.

However, an examiner needs to return the state to a state, for example, in which a fundus image with a wide angle of view can be imaged when imaging the other eye. Thus, the examiner possibly performs another photography without imaging a fundus image with a wide angle of view. Further, it is necessary to efficiently compare the image results of both of the eyes.

SUMMARY OF THE INVENTION

In light of the foregoing, an objective of the present invention is to improve the efficiency of an imaging operation when both eyes are imaged.

The present ophthalmic device includes a plurality of light sources including at least a light source for obtaining a return light of which aberration has been corrected with a correction unit from an eye under examination; and a control unit configured to control measurement lights from the light sources such that the measurement lights enter the eye under examination in a predetermined order when a photography of a second eye is started after a photography of a first eye has been completed.

Further features of the present invention will become apparent from the following description of exemplary embodiments (with reference to the attached drawings).

DESCRIPTION OF THE EMBODIMENTS

An exemplary embodiment of the present invention will be described with reference to the drawings. Note that the present invention is not limited to the embodiment to be described below and can variously be deformed and changed without departing from the gist of the invention.

Exemplary Embodiment

In the present exemplary embodiment, an AOSLO device applying the present invention will be described as an ophthalmic device. The AOSLO device includes an adaptive optical system in order to take a high lateral resolution planar image (hereinafter, sometimes referred to as an AOSLO image) of an eye fundus of an eye under examination.

To assist acquisition of an AOSLO image, the AOSLO device includes a WFSLO portion configured to take a planar image with a wide angle of view (hereinafter, sometimes referred to as a WFSLO image). Further, the AOSLO device includes an anterior eye portion observing portion for getting a position of incidence of a measurement light and a fixation lamp portion for inducing a line of sight in order to adjust a position to be imaged.

The AOSLO device according to the present exemplary embodiment obtains a planar image after correcting an optical aberration due to an eye under examination with a spatial light modulator, so that a good planar image can be obtained with reducing the effects of the eyepiece visibility of an eye to be examined and the optical aberration due to the eye to be examined.

Although the device includes an adaptive optical system in order to take a high lateral resolution planar image in the present exemplary embodiment, it is not necessary for the device to include an adaptive optical system as long as the device includes an optical system in which a high resolution can be implemented.

[Whole Structure of the Device]

Figure 1A:
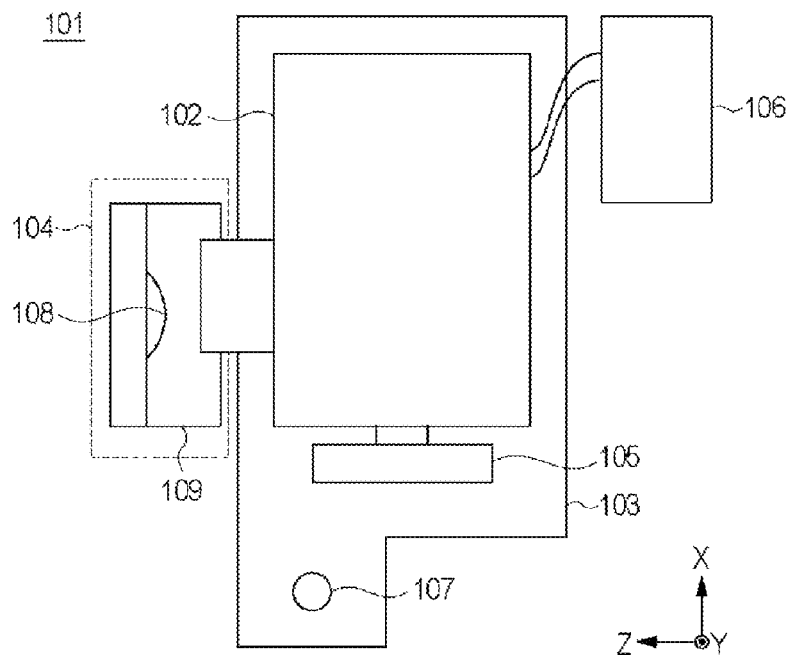
FIGS. 1A and 1B are views of examples of the whole structure of an AOSLO device according to an exemplary embodiment of the present invention.
Figure 1B:
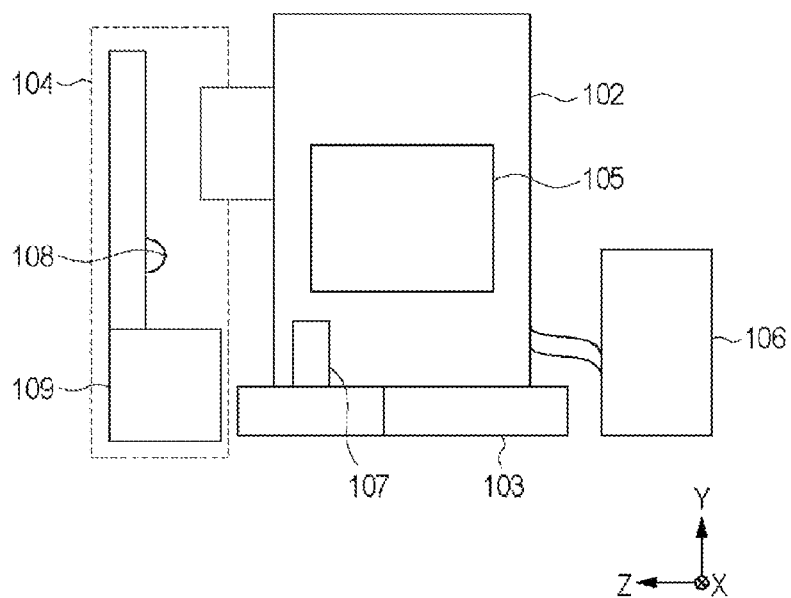

First, the schematic structure of an AOSLO device 101 according to the present exemplary embodiment will be described using FIGS. 1A and 1B. FIGS. 1A and 1B are views of examples of the whole structure of the AOSLO device 101 according to the present exemplary embodiment. FIG. 1A is a top face view of the AOSLO device 101 according to the present exemplary embodiment. FIG. 1B is a side face view of the AOSLO device 101 according to the present exemplary embodiment. Note that the AOSLO device 101 viewed from a face receiving portion 104 is the front face in the present exemplary embodiment.

The AOSLO device 101 includes a head portion 102, a stage portion 103, the face receiving portion 104, a liquid crystal monitor 105, a control PC 106, and a joystick 107.

The head portion 102, for example, includes a unit for imaging an eye under examination and a main optical system is embedded in the head portion. The embedded optical system will be described in detail below. Note that the head portion 102 is placed on the stage portion 103 in the present exemplary embodiment.

The stage portion 103 moves the head portion 102 in a horizontal direction and a vertical direction in response to the operation of the joystick 107 by an examiner. For example, inclining the joystick 107 moves the head portion 102 in a horizontal direction (X or Z-direction) and rotating the joystick 107 moves the head portion 102 in a vertical direction (Y-direction).

The face of a subject can be put on the face receiving portion 104, so that moving the face receiving portion 104 can adjust the position of the eye to be examined. Specifically, the face receiving portion 104 includes a jaw receiver 108 configured to put a jaw thereon, and a jaw receiver driving unit 109 configured to move the jaw receiver 108 with an electric-powered stage.

The liquid crystal monitor 105 can display various types of information and, for example, displays an operation screen of the AOSLO device 101. The liquid crystal monitor 105 is an exemplary display portion. Note that, although a liquid crystal monitor is used as the monitor in the present exemplary embodiment, the monitor is not limited to a liquid crystal monitor and the monitor can be any material that can display the information. Further, the liquid crystal monitor 105 can include a touch panel function.

The control PC 106 controls the whole of the AOSLO device 101.

The joystick 107 receives the instructions from the examiner. For example, inclining the joystick 107 moves the head portion 102 in a horizontal direction and rotating the joystick 107 moves the head portion 102 in a vertical direction. Note that, when the liquid crystal monitor 105 includes a touch panel function and the touch panel can move the head portion 102, it is not necessary to provide the joystick 107.

In this case, the liquid crystal monitor 105 is provided at the side surface of the head portion 102. However, it is not limited to the side surface and the liquid crystal monitor 105 can be provided at another position, for example, the rear surface of the head portion 102. Further, the position of the liquid crystal monitor 105 can fixedly or movably be structured. Further, although the control PC 106 is provided at the outside of the head portion 102, it is not limited to the outside and the control PC 106 can be provided at the inside of the head portion 102 or the stage portion 103. Further, although the joystick 107 is provided on the side surface of the head portion 102, it is not limited to the side surface and the joystick 107 can be provided at another position, for example, the rear surface of the head portion 102.

[Structure of the Optical System]

Figure 2:
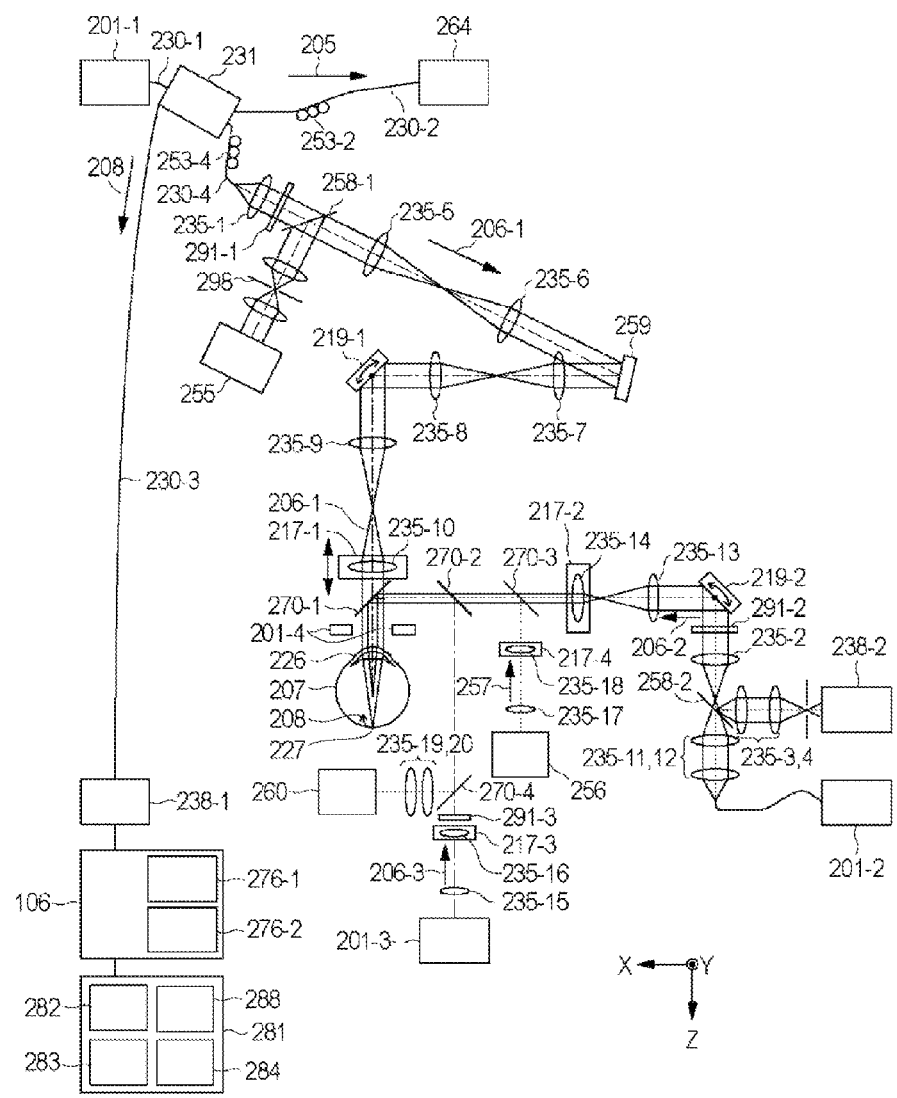
FIG. 2 is a view of an exemplary structure of an optical system of an AOSLO device according to an exemplary embodiment of the present invention.

Next, an optical system embedded in the head portion 102 will specifically be described using FIG. 2. Note that all of the optical system illustrated in FIG. 2 is not necessarily be embedded in the head portion 102. For example, the optical system illustrated in FIG. 2 can be embedded in the head portion 102 and the stage portion 103. FIG. 2 is a view of an exemplary structure of the optical system of the AOSLO device 101 in the present exemplary embodiment.

Note that, although the whole of the optical system mainly includes a refractive optical system using a lens in the present exemplary embodiment, the optical system can include a reflective optical system using a spherical mirror instead of a lens.

The optical system illustrated in FIG. 2 includes an AOSLO portion, a beacon portion, a WFSLO portion, a fixation lamp portion, and an anterior eye portion observing portion.

The AOSLO portion includes a light source 201-1, single mode fibers 230-1, 230-3, and 230-4, an optical fiber 230-2, an optical coupler 231, polarization controllers 253-2 and 253-4, and a shutter 291-1. In this case, a shutter 291-2 is an example of a first limitation unit for limiting the incidence of a first measurement light into the eye under examination and placed at the optical path connecting a second light source to the eye under examination. Further, the AOSLO portion includes lenses 235-1, 235-5, 235-6, 235-7, 235-8, 235-9, and 235-10, a beam splitter 258-1, a spatial light modulator 259, and an X and Y scanner 219-1. Further, the AOSLO portion includes a dichroic mirror 270-1, an electric-powered stage 217-1, a light quantity measurement apparatus 264, and a detector 238-1.

The beacon portion includes a light source 201-3, lenses 235-5, 235-6, 235-7, 235-8, 235-9, 235-10, 235-15, and 235-16, the X and Y scanner 219-1, the spatial light modulator 259, and a pinhole 298. Further, the beacon portion includes a shutter 291-3, the dichroic mirrors 270-1 and 270-2, the electric-powered stages 217-1 and 217-3, the beam splitter 258-1, and a wave-front sensor 255. In this case, the shutter 291-3 is an example of the first limitation unit for limiting the incidence of a second measurement light into the eye under examination and placed at the optical path connecting the first light source to the eye under examination.

The WFSLO portion includes a light source 201-2, lenses 235-2, 235-3, 235-4, 235-11, 235-12, 235-13, and 235-14, a beam splitter 258-2, and an X and Y scanner 219-2. Further, the WFSLO portion includes an electric-powered stage 217-2, the dichroic mirrors 270-1, 270-2, and 270-3, the shutter 291-2, and a detector 238-2.

The fixation lamp portion includes a fixation lamp 256, lenses 235-17 and 235-18, the dichroic mirrors 270-1, 270-2, and 270-3, and an electric-powered stage 217-4.

The anterior eye portion observing portion includes an anterior eye portion illuminating light source 201-4, the dichroic mirrors 270-1, 270-2, and 270-4, lenses 235-19 and 235-20, and a CCD camera 260.

[AOSLO Portion]

The AOSLO portion obtains an AOSLO image.

First, the light source 201-1 will be described. The light source 201-1 is a Super Luminescent Diode (SLD) that is a typical low coherent light source. As an example, the light ejected from the light source 201-1 has a center wavelength of 840 nm, a bandwidth (full width at half maximum) of 50 nm. The light source 201-1 is an example of the second light source ejecting the second measurement light. Here, a low coherent light source is selected in order to obtain a low speckle noise planar image. Although an SLD is selected in this case, any types of light sources that can emit a low coherent light can be used and, for example, an Amplified Spontaneous Emission (ASE) can also be used.

Further, For a measurement of an eye, a near-infrared light is suitable as the wavelength. Further, the wavelength affects the lateral resolution of the obtained planar image. Thus, the wavelength is desirably as short as possible. Although the wavelength is 840 nm as an example in this case, another wavelength can be selected depending on the part to be measured of the observation object.

The light emitted from the light source 201-1 is divided into a reference light 205 and a measurement light 206-1 in the proportion of 90 to 10 through the single mode fibers 230-1 and the optical coupler 231. Specifically, the light emitted from the light source 201-1 is divided into the reference light 205 and the measurement light 206-1 by the optical coupler 231. Note that the bifurcation ratio by the optical coupler 231 is not limited to the above-mentioned values.

[Reference Light 205]

Next, the reference light 205 will be described.

The reference light 205 divided by the optical coupler 231 enters the light quantity measurement apparatus 264 through the optical fiber 230-2 including a polarization controller 253-4 configured to control the polarization of a light. The light quantity measurement apparatus 264 measures the light quantity of the reference light 205 and the measured quantity is used for monitoring the light quantity of the measurement light 206-1. For example, when the value measured by the light quantity measurement apparatus 264 exceeds a predetermined threshold, the control PC 106 determines that the value exceeds a safe light quantity and limits the incidence of the light ejected from the light source 201-1 into the eye under examination.

[Measurement Light 206-1]

Next, an optical path of the measurement light 206-1 will be described.

The measurement light 206-1 divided by the optical coupler 231 is led to the lens 235-1 through a single mode fiber 230-4 including the polarization controllers 253-2 configured to control the polarization of a light. Then, the lens 235-1 causes the measurement light 206-1, for example, to be a parallel light having a beam diameter of 4 mm. Note that the value of the beam diameter is an example and the diameter is not limited to the value. After that, the measurement light 206-1 reaches the beam splitter 258-1 through the shutter 291-1. The shutter 291-1 can control whether to cause the light ejected from the light source 201-1 to enter an eye under examination 207.

The measurement light 206-1 enters the spatial light modulator 259 through the beam splitter 258-1 and the lenses 235-5 and 235-6. Note that the beam splitter 258-1 reflects, to the wave-front sensor 255, the light ejected from the light source 201-3 and returning from the eye under examination 207 while transmitting the light going to the eye under examination 207 from the light source 201-1 and the light ejected from the light source 201-1 and returning from the eye under examination 207. In other words, the beam splitter 258-1 transmits a light having a wavelength between 800 and 880 nm and reflects a light having another wavelength.

Further, although a reflective spatial light modulator is used as an aberration correction device in the present exemplary embodiment, a transmission spatial light modulator or a variable shape mirror can also be used.

Here, the spatial light modulator 259 is controlled by the control PC 106 through a spatial light modulator driver 288 in a driver portion 281. In other words, the spatial light modulator driver 288 is electrically connected to the spatial light modulator 259. Note that, although the driver portion 281 is provided at the outside of the control PC 106 in FIG. 2, the driver portion 281 can be provided at the inside of the control PC 106.

The measurement light 206-1 is modulated in the spatial light modulator 259, passes through the lenses 235-7 and 235-8, and enters a mirror of the X and Y scanner 219-1. Although the X and Y scanner 219-1 has a mirror for simplicity in this case, two mirrors of an X scanner and a Y scanner are actually placed adjacent to each other for a raster scan on a retina 227 in a direction perpendicular to the optical axis. Further, the center of the measurement light 206-1 is adjusted in such a way as to correspond to the rotational center of the mirrors of the X and Y scanner 219-1.

In this case, the X scanner scans the image with the measurement light 206-1 in the horizontal direction of the surface of the image and a resonance scanner is used as the X scanner in this case. For example, the X scanner has a driving frequency of about 7.9 kHz. On the other hand, the Y scanner scans the image with the measurement light 206-1 in the vertical direction of the surface of the image and a galvanometer scanner is used as the Y scanner in this case. The driving waveform is, for example, a saw-tooth wave. For example, the frequency is 32 Hz and the duty ratio is 16%. The driving frequency of the Y scanner is a critical parameter for determining the frame rate for taking an AOSLO image.

Here, the X and Y scanner 219-1 is controlled by the control PC 106 through an optical scanner driver 282 in the driver portion 281. In other words, the optical scanner driver 282 is electrically connected to the X and Y scanner 219-1.

The measurement light 206-1 used for the scan by the X and Y scanner 219-1 is led to the eye under examination 207 that is the observation object through the lenses 235-9 and 235-10 and the dichroic mirror 270-1. In other words, the AOSLO portion is an example of a second illumination optical system configured to illuminate an eye under examination by scanning the eye under examination with the second measurement light ejected from the second light source.

The lenses 235-9 and 235-10 are optical systems for scanning the retina 227 and have a role for scanning the retina 227 while taking the center of the pupil of the eye under examination 207 as the axis for the measurement light 206-1.

Although the measurement light 206-1 has a beam diameter of 4 mm in this case, the beam diameter can be increased in order to obtain a higher resolution optical image or can be less than 4 mm when a high resolution is not required. In other words, the beam diameter is not limited to 4 mm.

Further, 217-1 is an electric-powered stage that moves in a direction indicated by an arrow in the drawing and moves the position of the attached lens 235-10 and can adjust the focus.

The electric-powered stage 217-1 is controlled by the control PC 106 through an electric-powered stage driver 283 in the driver portion 281 in this case. In other words, the electric-powered stage driver 283 is electrically connected to the electric-powered stage 217-1. Adjusting the position of the lens 235-10 can bring the measurement light 206-1 into a predetermined layer of the retina 227 of the eye under examination 207 so that the eye can be observed. Further, this can be adopted even when the eye under examination 207 has a refractive error.

The measurement light 206-1 passed through the lens 235-10 enters the eye under examination through the dichroic mirror 270-1.

In this case, the dichroic mirror 270-1 transmits the light going to the eye under examination from the light source 201-1, the light ejected from the light source 201-1 and returning from the eye under examination, and the light ejected from the light source 201-3 and returning from the eye under examination. On the other hand, the dichroic mirror 270-1 reflects the light going to the eye under examination from the light source 201-2, the light ejected from the light source 201-2 and returning from the eye under examination, and the light ejected from the anterior eye portion illuminating light source 201-4 and returning from the eye under examination. The dichroic mirror 270-1 also reflects the light from the fixation lamp 256. Further, the dichroic mirror 270-1, for example, reflects the half of the light going to the eye under examination from the light source 201-3 and the light ejected from the light source 201-3 and returning from the eye under examination, and transmits the other half of them. Note that the ratio of the reflect and the transmission is not limited to 1:1. In other words, the dichroic mirror 270-1 has the properties for transmitting a light having a wavelength between 800 and 880 nm and transmitting the half of a light having a wavelength between about 750 and 770 nm and reflecting the other half. The dichroic mirror 270-1 can separate the lights ejected from the light source 201-1 and the light source 201-3 from the lights ejected from the other light sources.

After entering the eye under examination 207, the measurement light 206-1 becomes a return light 208 because of the reflect or scatter from the retina 227, goes back along the optical path and is led to the optical coupler 231 again. Then, the measurement light 206-1 reaches the detector 238-1 through the single mode fiber 230-3. In other words, the AOSLO portion is an example of a first imaging optical system configured to image an eye under examination using the return light of the second measurement light from the eye under examination. Further, the spatial light modulator 259 is an example of a correction unit for correcting the aberration of the return light of the second measurement light from the eye under examination using the aberration measured by a measuring optical system and placed at the first imaging optical system. For example, an Avalanche Photo Diode (APD) or a Photomultiplier Tube (PMT) that is a high-speed and high-sensitive optical sensor is used as the detector 238-1. However, the detector 238-1 is not limited to the sensors. The detector 238-1 converts the light intensity of the return light 208 into a voltage and the control PC 106 creates a planar image of the eye under examination 207 using the voltage signal. In other words, the detector 238-1 is an example of a first obtainment unit for obtaining a first image of the eye under examination using the aberration-corrected return light of the second measurement light from the eye under examination.

[WFSLO Portion]

Next, the WFSLO portion will be described. The WFSLO portion obtains a WFSLO image. Note that, for simplicity, the description for the parts overlapping with those in the AOSLO portion is not repeated here because the WFSLO portion basically has the same structure as the AOSLO portion.

The WFSLO portion includes a light source 201-2. The light source 201-2 is an SLD similarly to that of the AOSLO portion. The light ejected from the light source 201-2, for example, has a center wavelength of 920 nm and a bandwidth of 20 nm. The light source 201-2 is an example of a third light source ejecting a third measurement light. Note that any type of light source, for example, an Amplified Spontaneous Emission (ASE) can be used as long as a low coherent light can be emitted although the SLD is selected in this case. The wavelength and the bandwidth of the light ejected from the light source 201-2 are also not limited to the above-mentioned values and other values can also be selected.

The optical path of a measurement light 206-2 ejected from the light source 201-2 will be described. The measurement light 206-2 ejected from the light source 201-2 is led to an eye under examination 207 that is an observation object through the shutter 291-2, the lens 235-2, the lenses 235-11 to 235-14, the beam splitter 258-2, the X and Y scanner 219-2, the dichroic mirrors 270-1 to 207-3, and the like. In other words, this is an example of a third illumination optical system configured to scan an eye under examination with the third measurement light ejected from the third light source to illuminate the eye under examination. Note that the shutter 291-2 can control whether to cause the light ejected from the light source 201-3 to enter the eye under examination 207.

While transmitting the light going to the eye under examination from the light source 201-2, the beam splitter 258-2 reflects, to a detector 238-2, the light ejected from the light source 201-2 and returning from the eye under examination at that case. In other words, the WOSLO portion is an example of a second imaging optical system configured to image an eye under examination using the return light of the third measurement light from the eye under examination in order to determine the image pickup position by the first imaging optical system.

Further, the dichroic mirror 270-2 transmits the light going to the eye under examination from the light source 201-2, the light ejected from the light source 201-2 and returning from the eye under examination, and the light from a fixation lamp 256. On the other hand, the dichroic mirror 270-2 reflects the light going to the eye under examination from the light source 201-3 and the light ejected from the light source 201-3 and returning from the eye under examination. Further, the dichroic mirror 270-2 reflects the light ejected from an anterior eye portion illuminating light source 201-4 and returning from the eye under examination 207. In other words, the dichroic mirror 270-2 has the properties for reflecting a light having a wavelength between 700 and 880 nm and transmitting a light having another wavelength. The dichroic mirror 270-2 can separate the lights ejected from the light source 201-3 and the anterior eye portion illuminating light source 201-4 from the lights ejected from the light source 201-2 and the fixation lamp 256.

Further, the dichroic mirror 270-3 transmits the light going to the eye under examination from the light source 201-2, the light ejected from the light source 201-2 and returning from the eye under examination, and the light from the fixation lamp 256. On the other hand, the dichroic mirror 270-3 reflects the light going to the eye under examination from the fixation lamp 256 and the light ejected from the fixation lamp 256 and returning from the eye under examination. In other words, the dichroic mirror 270-3 has the properties for transmitting a light having a wavelength of 700 nm or more and reflecting a light having another wavelength. The dichroic mirror 270-3 can separate the light ejected from the fixation lamp 256 from the light ejected from the light source 201-2.

Note that, although the X and Y scanner 219-2 has a mirror for simplicity in FIG. 2, two mirrors of an X scanner and a Y scanner are actually placed adjacent to each other for a raster scan on a retina 227 in a direction perpendicular to the optical axis.

In this case, the X scanner that is a component of the X and Y scanner 219-2 scans the image with the measurement light 206-2 in the horizontal direction of the surface of the image and a resonance scanner is used as the X scanner in this case. For example, the X scanner has a driving frequency of about 3.9 kHz. On the other hand, the Y scanner scans the image with the measurement light 206-2 in the vertical direction of the surface of the image and a galvanometer scanner is used as the Y scanner in this case. The driving waveform is, for example, a saw-tooth wave. For example, the frequency is 15 Hz and the duty ratio is 16%. The driving frequency of the Y scanner is a critical parameter for determining the frame rate of a WFSLO image. Note that the X and Y scanner 219-2 is controlled by a control PC 106 through an optical scanner driver 282 in a driver portion 281. In other words, the optical scanner driver 282 is electrically connected to the X and Y scanner 219-2.

Although the optical system is configured such that the measurement light 206-2 has a beam diameter of 1 mm in this case, the beam diameter can be increased in order to obtain a higher resolution optical image or can be less than 1 mm when a high resolution is not required. In other words, the beam diameter is not limited to 1 mm.

After entering the eye under examination 207, the measurement light 206-2 becomes a return light 208 because of the reflect or scatter from the retina 227 and reaches the detector 238-2 through the dichroic mirrors 270-1 to 270-3, the lenses 235-13 and 235-14, the lenses 235-2 to 235-4, the X and Y scanner 219-2, the beam splitter 258-2, and the like.

[Beacon Portion]

Next, the beacon portion for measuring the aberration generating in the eye under examination 207 will be described.

The beacon portion includes a light source 201-3. The light ejected from the light source 201-3 has a center wavelength of 760 nm and a bandwidth of 20 nm. The light source 201-3 corresponds to the first light source ejecting the first measurement light. Note that the center wavelength and the bandwidth of the light ejected from the light source 201-3 are not limited to the above-mentioned values and other values can also be selected.

The measurement light 206-3 ejected from the light source 201-3 is led to the eye under examination 207 that is the observation object through a shutter 291-3, the lenses 235-15 and 235-16, and the dichroic mirrors 270-1, 270-2, and 270-4. In other words, the beacon portion is an example of a first illumination optical system configured to illuminate an eye under examination with the first measurement light ejected from the first light source. In this case, to avoid the reflect from a cornea 226, the measurement light 206-3 enters, for example, eccentrically from the center of the eye under examination 207. The shutter 291-3 can control whether to cause the light ejected from the light source 201-3 to enter the eye under examination 207.

While transmitting the light going to the eye under examination 207 from the light source 201-3, the dichroic mirror 270-4 reflects, to the CCD camera 260, the light ejected from the anterior eye portion illuminating light source 201-4 and returning from the eye under examination at that case. In other words, the dichroic mirror 270-4 has the properties for transmitting a light having a wavelength of 750 nm or more and reflecting a light having another wavelength. The dichroic mirror 270-4 can separate the light ejected from the anterior eye portion illuminating light source 201-4 from the light ejected from the light source 201-3.

A part of the return light 208 of the light source 201-3 enters a wave-front sensor 255 through the beam splitter 258-1 and the pinhole 298 in order to measure the aberration of the return light 208 generated due to the eye under examination 207. In other words, the wave-front sensor 255 is an example of an aberration measurement unit for measuring the aberration due to the eye under examination using the return light of the first measurement light from the eye under examination. Further, the beacon portion is an example of a measuring optical system configured to measure the aberration due to the eye under examination using the return light of the first measurement light from the eye under examination. In this case, the pinhole 298 is placed in order to block an unnecessary light except for the return light 208. Note that the wave-front sensor 255 is electrically connected to the control PC 106.

The wave-front sensor 255 is a Shack-Hartmann wave-front sensor and the measurement range is, for example, from −10 D to 5 D. The obtained aberration is expressed using a Zernike polynomial to indicate the aberration due to the eye under examination 207. The Zernike polynomial includes the tilt (gradient) item, the de-focusing item, the astigma (astigmatism) item, the coma item, and the trefoil item.

The lenses 235-5 to 235-10 and the like are placed such that the cornea 226, the X and Y scanner 219-1, the wave-front sensor 255, and the spatial light modulator 259 are optically conjugated. Thus, the wave-front sensor 255 can measure the aberration due to the eye under examination 207. Further, the spatial light modulator 259 can correct the aberration due to the eye under examination 207.

[Fixation Lamp Portion]

A light flux 257 from the fixation lamp 256 has a role for enhancing the fixation or rotation of the eye under examination 207.

Figure 3:
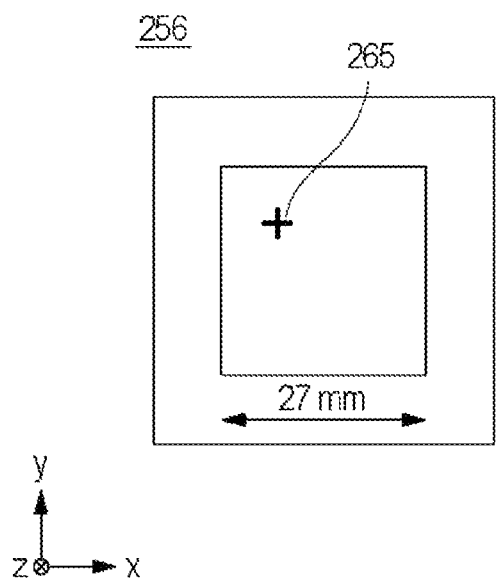
FIG. 3 is a view of an exemplary fixation lamp according to an exemplary embodiment of the present invention.

The fixation lamp 256 includes a luminescent display module and has a display surface (27 mm, 128×128 pixel) on the X and Y flat surface. In this case, a liquid crystal display, an organic EL display, an LED array display, or the like can be used. When the eye under examination 207 gazes the light flux 257 from the fixation lamp 256, the fixation or rotation of the eye under examination 207 is enhanced. For example, a cross-shaped pattern is displayed with blinking at a predetermined lighting position 265 on the display surface of the fixation lamp 256 as illustrated in FIG. 3.

The light flux 257 from the fixation lamp 256 is led to the retina 227 through the lenses 235-17 and 235-18, and the dichroic mirrors 270-1 to 270-3. Further, the lenses 235-17 and 235-18 are placed such that the display surface of the fixation lamp 256 and the retina 227 are optically conjugated. Further, the fixation lamp 256 is controlled by the control PC 106 through a fixation lamp driver 284 in the driver portion 281. In other words, the fixation lamp driver 284 is electrically connected to the fixation lamp 256.

Note that the size and the number of pixels of the display surface of the fixation lamp 256 are not limited to the above-mentioned values and other values can be selected. Further, although the pattern has a cross shape in the above-mentioned example, the pattern for the fixation is not limited to the shape and can have another shape.

[Anterior Eye Portion Observing Portion]

Next, the anterior eye portion observing portion will be described. The anterior eye portion observing portion obtains an image of the anterior eye portion of an eye under examination.

An anterior eye portion illuminating light source 201-4 is, for example, a Light Emitting Diode (LED) having a center wavelength of 740 nm. The light irradiated from the anterior eye portion illuminating light source 201-4 illuminates an eye under examination 207. The reflected light enters the CCD camera 260 through the dichroic mirrors 270-1, 270-2, and 270-4, and the lenses 235-19 and 235-20.

[Focus and Astigmatism Correction]

As described above, the optical system embedded in the head portion 102 includes the AOSLO portion, the WFSLO portion, the beacon portion, the fixation lamp portion, and the anterior eye portion observing portion. Among them, the AOSLO portion, the WFSLO portion, the beacon portion, and the fixation lamp portion include the electric-powered stages 217-1 to 217-4, respectively. The four electric-powered stages are coordinated with each other. However, when it is necessary to separately adjust each of the focus positions, separately operating each of the electric-powered stages can adjust each of them.

Further, the lens 235-10 is replaceable so that a spherical lens or a cylindrical lens can also be used depending on the aberration (refractive error) in the eye under examination 207. Further, not only a lens but also a plurality of lenses can be combined and installed.

[Shutter]

The AOSLO portion, the WFSLO portion, and the beacon portion include shutters 291-1 to 291-3 on the optical paths of the light sources 201-1 to 201-3, respectively in order to separately block each of the beams. This can control whether to cause each of the beams to enter the eye under examination 207. The control PC 106 (drive and control unit 114) controls the opening and closing of the shutters 291-1 to 291-3. Here, the shutters 291-1 to 291-3 are examples of limitation units included in a plurality of optical paths connecting a first light source, a second light source, and a third light source to the eye under examination, respectively. In other words, the drive and control unit 114 that is a control unit switches the incidence of a measurement light source into the eye under examination and the limitation on the incidence by controlling the limitation unit. Specifically, the drive and control unit 114 that is a control unit switches the incidence of the measurement light source into the eye under examination and the limitation on the incidence by controlling the opening and closing of the shutters while the first light source, the second light source, and the third light source are lighted. Note that the shutters 291-1 to 291-3 are examples of a first shutter, a second shutter, and a third shutter, respectively. In other words, the drive and control unit 114 is an example of the control unit for controlling the opening and closing of the first shutter, the second shutter, and the third shutter such that one of the first shutter, the second shutter, and the third shutter is opened and the other two shutters are closed while the first light source, the second light source, and the third light source are lighted.

Note that, although a shutter is used in order to control the beam entering the eye under examination 207 in the present exemplary embodiment, the control is not limited to using the shutter. Changing the optical path with a mirror or the like can also control the beam entering the eye under examination 207. Further, directly turning ON/OFF the light sources 201 can also control the beam entering the eye under examination 207. Further, providing an attenuation filter instead of the shutter and inserting the filter into the optical path and removing the filter from the optical path can switch the incidence of the measurement light source into the eye under examination 207 and the limitation on the incidence. Here, each of the mirror and the filter is an example of a limitation unit. Note that, when the limitation unit is a filter, the drive and control unit that is a limitation unit inserts the filter into the optical path and removes the filter from the optical path while the first light source, the second light source, and the third light source are lighted. This switches the incidence of the measurement light source into the eye under examination and the limitation on the incidence. Similarly, turning ON/OFF the light source 201-4 and the luminescent display module can control can control the anterior eye portion observing portion and the fixation lamp portion. Similarly, turning ON/OFF the light source 201-4 and the fixation lamp 256 can control the anterior eye portion observing portion and the fixation lamp portion. Note that, when the shutters 291-1 to 291-3 are used, the incidence of the light into the eye under examination 207 can be controlled while the light sources 201-1 to 201-3 are lighted. Thus, when the limitation on the incidence of the measurement light into the eye under examination 207 is lifted, the time to stably eject the light after the light sources 201-1 to 201-3 have been turned off is not required. This enables a prompt control. Note that the same is true in using the mirror or the filter.

The states of the opening and closing of the shutters 291-1 to 291-3 are displayed on a shutter state display region 509 of the control software screen (FIG. 5) by a display control unit 112 to be described below. The examiner clearly and easily knows which measurement light 206-1, 206-2, or 206-3 irradiates the eye under examination 207 from the display of the states of the opening and closing of the shutters. This improves the certainty of the imaging operation.

[Wavelength of Each Light Source]

Figure 4:
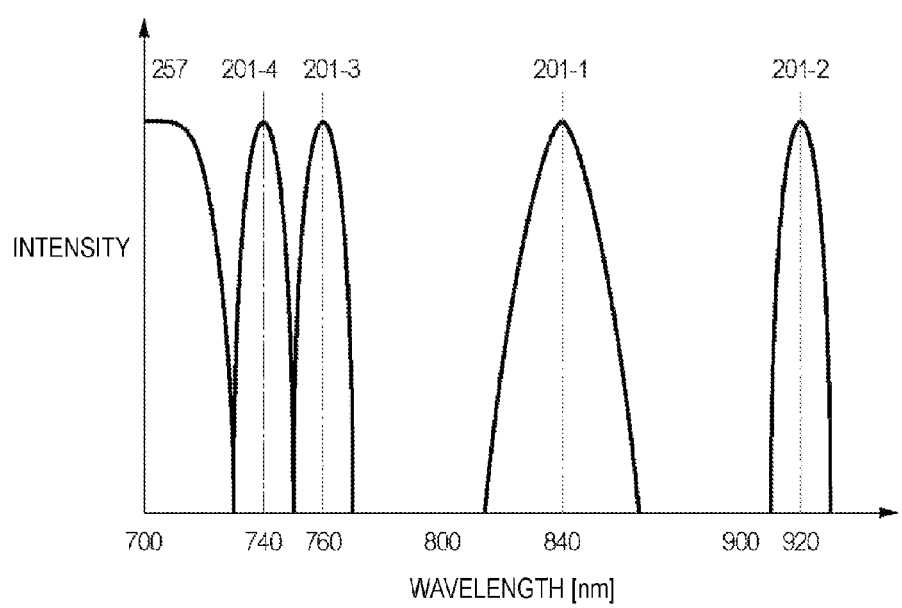
FIG. 4 is a view of an exemplary wavelength distribution of a measurement light of an AOSLO device according to an exemplary embodiment of the present invention.

FIG. 4 illustrates an exemplary wavelength distribution of the light sources used for the AOSLO portion, the WFSLO portion, the beacon portion, the fixation lamp portion, and the anterior eye portion observing portion. To divide the lights into the dichroic mirrors 270-1 to 270-4, respectively, each of the lights has a different wavelength band.

To reduce the dizziness given to the eye under examination, the lights ejected from the light sources 201-1 to 201-4 are desirably infrared lights having a wavelength of 700 nm or more. The light quantity of the light source 201-3 at the beacon portion can be lower than those of the other light sources because a high image quality is not required of the light source 201-3 and it is only necessary to obtain a Hartmann image. Thus, the wavelength of the light ejected from the light source 201-3 has a relatively small effect on the subject even if the wavelength is close to the visible light region. Accordingly, the wavelength of the light ejected from the light source 201-3 can be close to the visible light region. Further, the lights ejected from the light sources 201-1 to 201-4 preferably have a wavelength of 1000 nm or less because a silicon sensor is generally used as the detectors 238-1 and 238-2 and the silicon sensor has an extremely reduced sensitivity when the wavelength is around 1000 nm. An objective of the AOSLO device 101 is to obtain an AOSLO image and thus a WFSLO image is used as a subsidiary to obtain a desired AOSLO image. Thus, the wavelength of the light ejected from the light source 201-1 is reduced to shorter than the wavelength of the light ejected from the light source 201-2 in order to finally obtain a desired AOSLO image with a high resolution.

Thus, when the AOSLO device 101 is used for observing an eye fundus, the wavelengths should be arranged in the order of the beacon portion, the AOSLO portion, and the WFSLO portion from the short wavelength side and the center wavelengths of the wavelengths should be placed at intervals such that the dichroic mirrors easily divide the lights. In other words, the first measurement light has a center wavelength of 700 nm or more and the third measurement light has a center wavelength of 1000 nm or less.

Further, an image of the anterior eye portion obtained using the light ejected from the anterior eye portion illuminating light source 201-4 is used for adjusting the initial position of the head portion 102. Note that the position of the head portion 102 is also adjusted while the WFSLO image is watched. On the other hand, the light ejected from the light source 201-3 is used for measuring the aberration necessary to finally obtain a desired AOSLO image with a high resolution. Thus, the light quantity of the light source 201-3 is more than that of the anterior eye portion illuminating light source 201-4 to measure the aberration with high accuracy. Therefore, the wavelength of the light source 201-3 is increased to longer than that of the anterior eye portion illuminating light source 201-4. This can measure the aberration with high accuracy as reducing the subject's burden. In other words, the fourth measurement light has a center wavelength of 700 nm or more and the third measurement light has a center wavelength of 1000 nm or less.

In this case, the interval between the center wavelengths is desirably more than double for the sum of the halves of the full width at half maximums of the light sources next to each other. In the present exemplary embodiment, the interval between the center wavelengths of the light source 201-1 and the light source 201-2 is set at 80 nm (it is more than 70 nm that is double of 25+10 nm). This can reduce the loss of each of the lights as much as possible. Hereinafter, the method for determining the wavelengths including the process for determining the wavelengths will be described in detail. On the assumption that a wavelength distribution is generally a Gaussian distribution, the width of the Gaussian distribution at the half position of the peak (intensity peak) of the Gaussian distribution is referred to as a full width at half maximum and the intensity at the position having a width double of the full width at half maximum becomes one sixteenth of the peak value of the Gaussian distribution. In other words, 95% or more of the whole light quantity is included in the area where the width of the Gaussian distribution is less than double of the full width at half maximum. Thus, as described above, the interval between the center wavelengths is set at a value more than double for the sum of the halves of the full width at half maximums of the light sources next to each other. This can prevent the wavelengths from easily overlapping with each other between the light sources. Further, when the interval between the center wavelengths is set at double for the sum of the halves of the full width at half maximums of the light sources next to each other, the interval between the center wavelengths can be reduced as the wavelengths are prevented from overlapping with each other between the light sources. This can efficiently use the wavelengths. Thus, the wavelengths as short as possible can be used in order to increase the resolution.

Further, although the interval between the center wavelengths is more than double for the sum of the halves of the full width at half maximums of the light sources next to each other in the above-mentioned example, the interval is not limited to the above. For example, the value can be more than n times for the sum of one nths of the full width at half maximums of the light sources next to each other as the n is a natural number. Note that n=2 holds in the above-mentioned example. In other words, the interval between the center wavelengths is determined based on the value n times for the sum of one nths (the n is a natural number) of the full width at half maximums of a plurality of light sources next to each other. Specifically, the interval between the center wavelengths is more than a value n times for the sum of one nths of the full width at half maximums of a plurality of measurement light sources next to each other.

Note that the wavelength width used for determining the interval between the center wavelengths is not necessary to be a full width at half maximum. A given wavelength width can also be used. For example, to omit the division, the half wavelength width of the full width at half maximum can be used from the beginning or a wavelength width near the full width of the wavelength can be used. In other words, the interval between the center wavelengths can be determined based on each of the wavelength widths of a plurality of measurement light sources next to each other.

Further, the overlap of the wavelengths between the light sources is increased in the case in which the interval between the center wavelengths is set at a value double for the sum of the halves of the full width at half maximums of the light sources next to each other in comparison with the interval between the center wavelengths is set at a value more than double for the sum of the halves of the full width at half maximums of the light sources next to each other. At that case, an attenuation filter for attenuating the wavelength at the overlapping area can be provided such that the overlap of the wavelengths has a reduced effect. For example, the narrower the interval between the center wavelengths is, the more the wavelengths overlap with each other. Thus, an attenuation filter that attenuates the wavelengths over a wider area as the interval between the center wavelengths becomes narrower can be used. Note that a table linking the interval between the center wavelengths to the wavelength range to be attenuated is provided and the control PC 106 refers to the table such that an attenuation filter (not illustrated in the drawings) is inserted into or removed from a given position in the optical path, for example, before the eye under examination 207 or in the optical path of each of the light sources. Using an attenuation filter in such a manner can cause the center wavelengths to be closer to each other and thus can more efficiently use the wavelengths.

Note that FIG. 4 illustrates the difference between the wavelengths of the light sources and does not prescribe the intensities and the spectral forms.

[Imaging]

Next, the method for creating an image.

The light intensity of the entered light is converted into a voltage in the detector 238-1. The voltage signal obtained in the detector 238-1 is converted into a digital value at an AD board 276-1 in the control PC 106 to perform data processing synchronized with the operation of the X and Y scanner 219-1 and the driving frequency. Then an AOSLO image is formed. At that time, the AD board 276-1 has an uptake speed of 15 MHz. Similarly, the voltage signal obtained in the detector 238-2 is converted into a digital value at an AD board 276-2 in the control PC 106 and a WFSLO image is formed in the control PC 106.

[Control PC 106]

Figure 5:
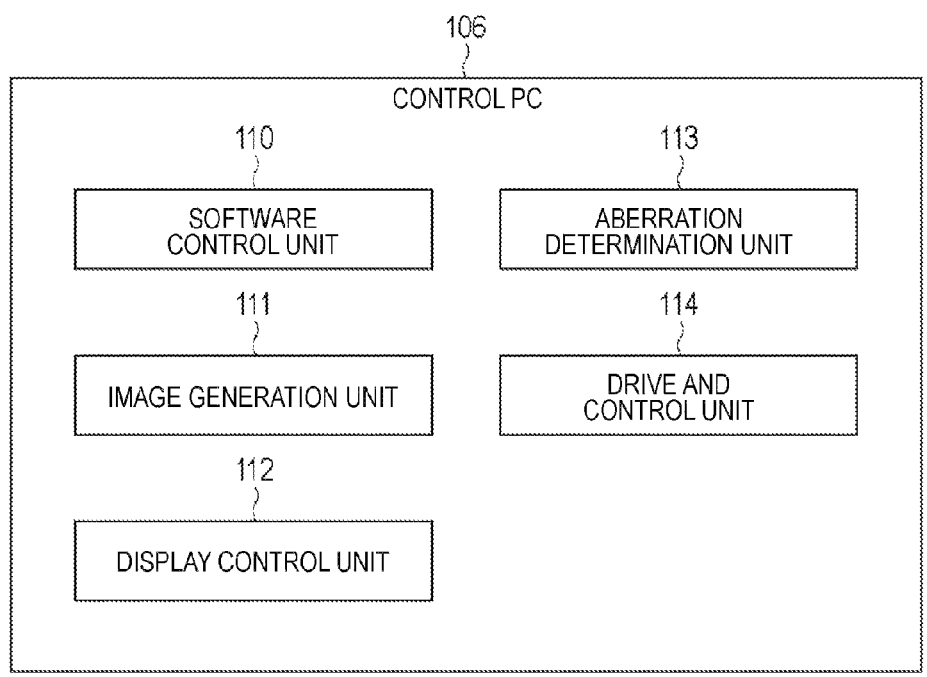
FIG. 5 is a schematic view of an exemplary function of a control PC.

An exemplary function of the control PC 106 will be described. FIG. 5 is a schematic view of an exemplary function of the control PC 106.

The control PC 106 works as a software control unit 110, an image generation unit 111, the display control unit 112, an aberration determination unit 113, and a drive and control unit 114 as the processing portion such as a CPU executes a predetermined program stored in a storage device 800 working as a storage unit such as a memory.

The software control unit 110 controls the start and the stop of control software for measurement and viewer software. For example, the software control unit 110 starts the control software for measurement when the power of the AOSLO device 101 is activated or when the examiner designates an execute file of the control software. Further, the software control unit 110 starts the viewer software when the examiner designates an execute file of the viewer software. Furthermore, the software control unit 110 stops the control software for measurement and the viewer software when receiving the instruction for termination of the software from the examiner. Note that the control software and the viewer software can be stored in the storage device 800 such as a memory included in the control PC 106 or can be stored in an external storage unit 800 capable of communicating with the control PC 106 through radio or a wire.

The image generation unit 111 generates various images. For example, the image generation unit 111 generates an AOSLO image based on the output of the AD board 276-1. Further, the image generation unit 111 generates a WFSLO image based on the output of the AD board 276-2. Further, the image generation unit 111 generates a Hartmann image based on the output of the wave-front sensor 255. Further, the image generation unit 111 generates an image of an anterior eye portion based on the output of the CCD camera 260.

The display control unit 112 displays various types of information, for example, about the image generated by the image generation unit 111 on the liquid crystal monitor 105. Further, a display control unit displays a graph or a value of the aberration determined by the aberration determination unit 113 on the liquid crystal monitor 105.

Further, the display control unit 112 displays the states of the opening and closing of the shutters 291-1 to 291-3 on the shutter state display region 509.

In this case, the information displayed on the shutter state display region 509 is not limited to the states of the opening and closing of the shutters. For example, the information indicating the state of incidence of the measurement light into the eye under examination can be displayed. If a filter is used instead of the shutter, the information indicating whether the filter is inserted into or removed from the optical path can be displayed. Alternatively, the information indicating whether the measurement light enters can be displayed. In other words, the display control unit 112 is an example of a display control unit for displaying, on a display portion, the display form indicating the states of the incidence of the first measurement light, the second measurement light, and the third measurement light into the eye under examination. More specifically, the display control unit 112 displays a display form indicating the state of the opening and closing of the shutter included in each of a plurality of optical paths on a display portion. Further, the display control unit 112 displays, on a display portion, a display form indicating the insertion and the removal of the filter included in each of a plurality of optical paths.

The aberration determination unit 113 determines the aberration in the eye under examination 207 based on the output of the wave-front sensor 255. Specifically, the aberration determination unit 113 determines the aberration in the eye under examination 207 from the Hartmann image.

The drive and control unit 114 drives various movable members. Specifically, the drive and control unit 114 drives the X and Y scanners 219-1 and 219-2 through the optical scanner driver 282. Further, the drive and control unit 114 drives the electric-powered stages 217-1 to 217-4 through the electric-powered stage driver 283. Further, the drive and control unit 114 drives the fixation lamp 256 through the fixation lamp driver 284. Specifically, the drive and control unit 114 controls the movement, the switch between lighting and blinking, and the change of the size or the shape of the lighting position 265. Further, the drive and control unit 114 controls the spatial light modulator 259 through the spatial light modulator driver 288. Specifically, the drive and control unit 114 corrects the aberration due to the eye under examination 207 by controlling the spatial light modulator 259 based on the aberration determined by the aberration determination unit 113. More specifically, the drive and control unit 114 controls the spatial light modulator 259 in order to reduce the aberration. In other words, the spatial light modulator 259 is an example of a correction unit for correcting the aberration of the return light of the second measurement light from the eye under examination generated in the eye under examination based on the aberration measured by an aberration measurement unit.

Further, the drive and control unit 114 drives the jaw receiver 108 through the jaw receiver driving unit 109 in response to the input by the examiner.

Further, the drive and control unit 114 controls the opening and closing of the shutters 291-1 to 291-3. Further, the drive and control unit 114 controls the turn on and off of the light source. The drive and control unit 114 controls the first control unit and the second control unit while the first light source and the second light source are lighted. The drive and control unit 114 is an example of a control unit for causing one of the first measurement light or the second measurement light to enter the eye under examination and limiting the incidence of the other measurement lights into the eye under examination.

[Imaging Process]

Figure 6:
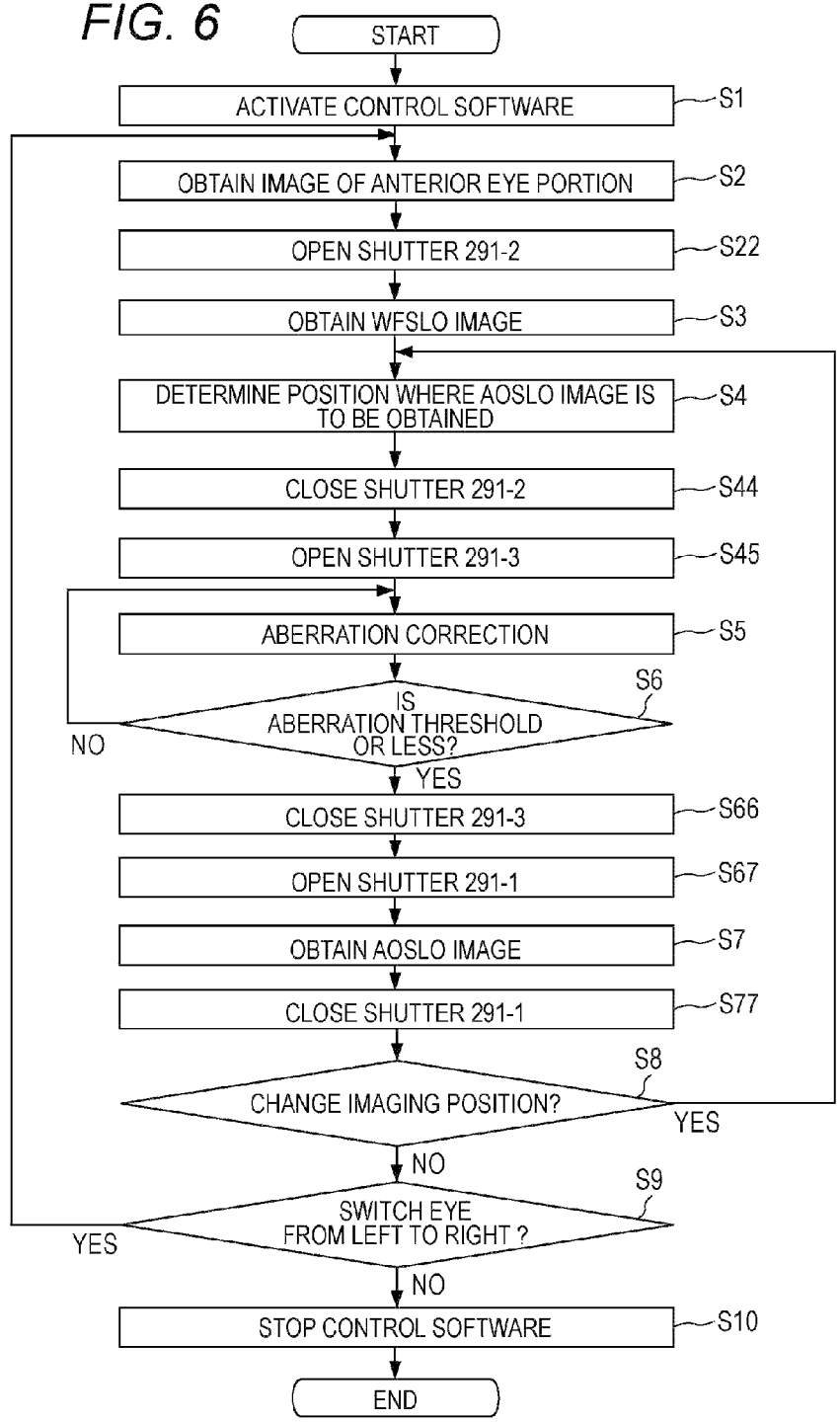
FIG. 6 is a flowchart of an example of an imaging process with an AOSLO device according to an exemplary embodiment of the present invention.
Figure 7:
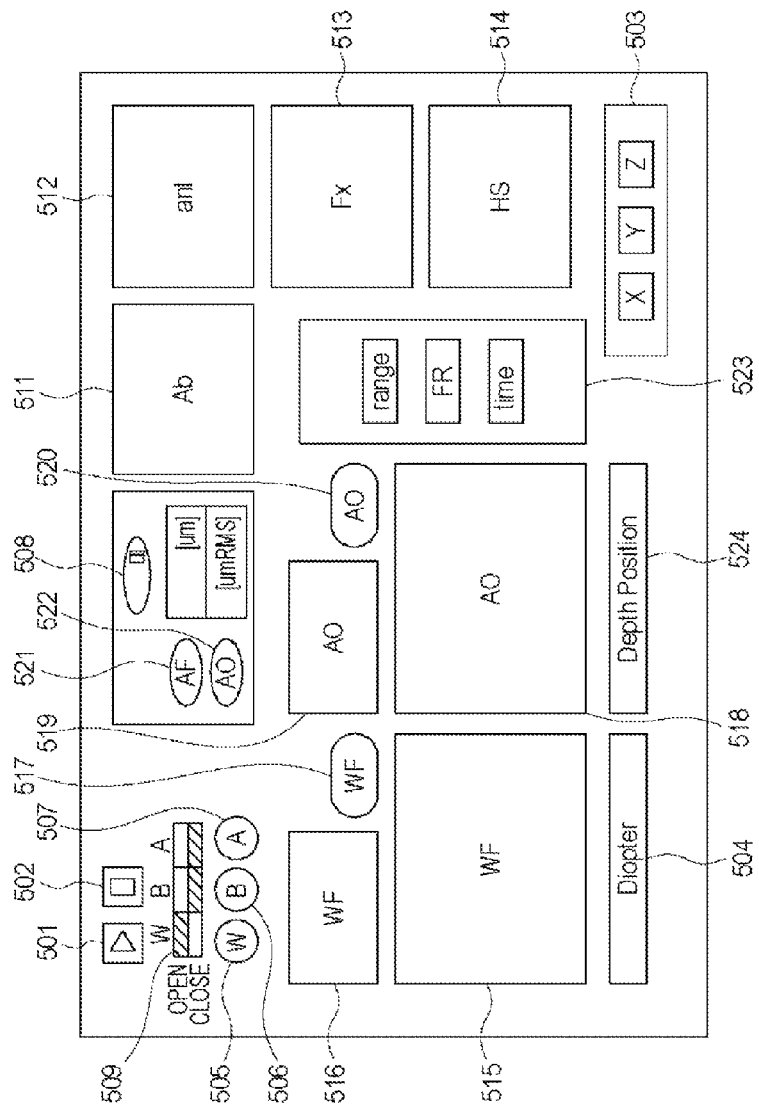
FIG. 7 is a view of an exemplary structure of a control software screen in an AOSLO device according to an exemplary embodiment of the present invention.

Next, the imaging process at the AOSLO device 101 in the present exemplary embodiment will be described with reference to FIGS. 6 and 7. FIG. 6 is a flowchart of an exemplary operation of the AOSLO device in the present exemplary embodiment. FIG. 7 is a view of an exemplary control screen of the AOSLO device 101 displayed on the liquid crystal monitor 105 in the present exemplary embodiment.

Hereinafter, each procedure in the flowchart will be described in detail. Note that all of the shutters 291-1 to 291-3 are closed at the initial state.

First, activating the power of the AOSLO device 101 including the control PC 106 starts each procedure by the AOSLO device 101.

[Step S1]

Once the power of the AOSLO device 101 including the control PC 106 is activated, the software control unit 110 starts the control software for measurement. When the control software for measurement is started, the display control unit 112 displays a control software screen illustrated in FIG. 7 on the liquid crystal monitor 105. Note that, after the control software for measurement is started, the subject sets his or her face on the face receiving portion 104.

Here, an exemplary control screen illustrated in FIG. 7 will be described. Note that the screen structure of the control software illustrated in FIG. 7 is an example and the structure is not limited to the example illustrated in FIG. 7. In other words, the arrangement of the control screen or the like can arbitrarily be changed.

The control screen illustrated in FIG. 7 includes an execute button 501, a STOP button 502, an electric-powered stage travel button 503, a focus adjustment button 504, a WFSLO measurement button 505, an aberration measurement button 506 and an AOSLO measurement button 507.

Further, the control screen illustrated in FIG. 7 includes an aberration correction suspending button 508, the shutter state display region 509, an aberration display region 511, an anterior eye portion display region 512, a fixation lamp position display region 513, a wave-front display region 514, and a WFSLO display region 515.

Further, the control screen illustrated in FIG. 7 includes a WFSLO strength display region 516, a WFSLO recording button 517, an AOSLO display region 518, an AOSLO strength display region 519, an AOSLO recording button 520, and an autofocus button 521.

Further, the control screen illustrated in FIG. 7 includes an aberration correction button 522, an imaging condition setting button 523, and a depth adjustment button 524.

After the execute button 501 is selected (for example, clicked) with an instruction unit such as a mouse, the drive and control unit 114 turns on the anterior eye portion illuminating light source 201-4 and the light ejected from the anterior eye portion illuminating light source 201-4 enters the eye under examination 207. Then, the display control unit 112 displays the image of the anterior eye portion generated based on the output of the CCD camera 260 on the anterior eye portion display region 512.

Note that, when the execute button 501 is selected, the control PC 106 can display the screen for selecting or registering the patient information on the liquid crystal monitor 105. In this case, after the patient information is selected or registered, the anterior eye portion illuminating light source 201-4 is turned on and the display control unit 112 can display the image of the anterior eye portion on the anterior eye portion display region 512. Note that the selection by the instruction unit is not limited to a click. When the liquid crystal monitor 105 includes a touch panel function, the examiner can touch the monitor for selecting.

When the STOP button 502 is selected, the software control unit 110 in the control PC 106 stops the control software.

The electric-powered stage travel button 503 includes an X stage travel button, a Y stage travel button, and a Z stage travel button. When the electric-powered stage travel button 503 is selected, the drive and control unit 114 moves the jaw receiver 108 through the jaw receiver driving unit 109. For example, each of the X stage travel button, the Y stage travel button, and the Z stage travel button is a slider and the drive and control unit 114 moves the jaw receiver 108 according to the travel distance and the travel direction of the slider. For example, when the Y stage travel button is selected, the drive and control unit 114 moves the jaw receiver 108 in a Y-direction. Similarly, the drive and control unit 114 moves the jaw receiver 108 in an X-direction or a Z-direction according to the selected button. Note that the electric-powered stage travel button 503 is not limited to a slider and anther configuration can be used as long as the configuration can give the instruction for driving to the jaw receiver 108.

The focus adjustment button 504, for example, is a slider and the drive and control unit 114 drives the lenses 235-10, 235-14, 235-16, and 235-18 according to the travel distance and the travel direction of the slider. Note that the focus adjustment button 504 is not limited to a slider and another configuration can be used as long as the configuration can give the instruction for driving to the lenses 235-10, 235-14, 235-16, and 235-18.

When the WFSLO measurement button 505 is selected, the control PC 106 allows the light ejected from the light source 201-2 to enter the eye under examination. Specifically, the state in which the incidence of the lights ejected from the light sources 201-1 to 201-3 into the eye under examination has been limited before the WFSLO measurement button 505 has been selected is switched to the state in which the light ejected from the light source 201-enters the eye under examination. The switch is performed as the drive and control unit 114 turns on the light source 201-2 that has been turned off or removes the shutter that has been inserted into the optical path connecting the eye under examination to the light source 201-2 from the optical path.

When the aberration measurement button 506 is selected, the drive and control unit 114 limits the incidence of the light ejected from the light source 201-2 into the eye under examination. Limiting the incidence of the ejected light to the eye under examination 207 is caused by closing the shutter 291-2 in the optical path connecting the eye under examination 207 to the light source 201-2 or by turning off the light source 201-2. Further, when the aberration measurement button 506 is selected, the control PC 106 allows the light ejected from the light source 201-3 to enter the eye under examination 207. Specifically, the state in which the incidence of the lights ejected from the light sources 201-1 and 201-3 into the eye under examination has been limited before the aberration measurement button 506 has been selected is switched to the state in which the light ejected from the light source 201-3 enters the eye under examination. The switch is performed, for example, as the drive and control unit 114 turns on the light source 201-3 that has been turned off or opens the shutter 291-3 that has been inserted into the optical path connecting the eye under examination 207 to the light source 201-3 from the optical path. Note that both of the timing of limiting the incidence of the light ejected from the light source 201-2 into the eye under examination 207 and the timing of allowing the incidence of the light ejected from the light source 201-3 into the eye under examination 207 can be first, or at the same time. However, allowing the incidence of the light ejected from the light source 201-3 into the eye under examination 207 preferably comes after the limitation of the incidence of the light ejected from the light source 201-2 into the eye under examination 207 in such a way as to minimize the quantity of the light entering the eye under examination 207.

When the AOSLO measurement button 507 is selected, the drive and control unit 114 limits the incidence of the light ejected from the light source 201-3 into the eye under examination. Limiting the incidence of the ejected light into the eye under examination 207, for example, is caused by closing the shutter 291-3 in the optical path connecting the eye under examination 207 to the light source 201-3 or by turning off the light source 201-3. Further, when the AOSLO measurement button 507 is selected, the control PC 106 allows the light ejected from the light source 201-1 to enter the eye under examination 207. Specifically, the state in which the incidence of the lights ejected from the light sources 201-1 and 201-2 into the eye under examination 207 has been limited before the AOSLO measurement button 507 has been selected is switched to the state in which the light ejected from the light source 201-1 enters the eye under examination 207. The switch is performed, for example, as the drive and control unit 114 turns on the light source 201-1 that has been turned off or opens the shutter 291-1 that has been inserted into the optical path connecting the eye under examination 207 to the light source 201-1 from the optical path. Note that both of the timing of limiting the incidence of the light ejected from the light source 201-3 into the eye under examination 207 and the timing of allowing the incidence of the light ejected from the light source 201-1 into the eye under examination 207 can be first, or at the same time. However, allowing the incidence of the light ejected from the light source 201-1 into the eye under examination 207 preferably comes after limiting the incidence of the light ejected from the light source 201-3 into the eye under examination 207 in such a way as to minimize the quantity of the light entering the eye under examination 207.

When the aberration correction suspending button 508 is selected, the control PC 106 suspends the aberration correction. For example, the drive and control unit 114 is stopped from controlling the spatial light modulator 259 although the aberration determination unit 113 continues calculating the aberration. Alternatively, the calculation of the aberration is stopped. Note that a resumption button (not illustrated in the drawings) can be provided such that the aberration correction is resumed when the resumption button is selected. When the aberration correction suspending button 508 is selected again, the aberration correction can be resumed.

The information indicating the states of the opening and closing of the shutters 291-1 to 291-3 are displayed on the shutter state display region 509 by the display control unit 112. In the example illustrated in FIG. 7, a region for showing whether each of the shutters 291-1 to 291-3 is opened (in the drawing, referred to as OPEN) or closed (in the drawing, referred to as CLOSE) is provided. Then, the region is highlighted in response to the states of the opening and closing of the shutters 291-1 to 291-3. For example, in the state illustrated in FIG. 7, the shutter 291-1 is opened and the shutters 291-2 and 291-3 are closed. Note that the configuration of the shutter state display region 509 is not limited to the above and anther configuration can be used as long as the display configuration can confirm the opening or the closing of the shutters 291-1 to 291-3. For example, a switch corresponding to each of the shutters 291-1 to 291-3 can be displayed such that the switch is pushed down when the shutter is opened and the switch is not pushed down when the shutter is closed.

The aberration determined (calculated) by the aberration determination unit 113 is displayed as a time-series graph on the aberration display region 511 by the display control unit 112. In this case, the value of the aberration when the AOSLO measurement button 507 is selected is especially stored in the storage unit 800. The coordinate position of the fixation is linked to the fixation lamp position display region 513 to be described below.

When the AOSLO measurement button 507 is selected, the display position of the fixation lamp at the photography, the aberration calculated by the aberration determination unit 113, and the imaged eye (the right eye or the left eye) are stored in the storage unit 800 while linked to each other.

The image of the anterior eye portion generated by the image generation unit 111 according to the output of the CCD camera 260 is displayed on the anterior eye portion display region 512 by the display control unit 112.

The information indicating the position of the fixation is displayed on the fixation lamp position display region 513 by the display control unit 112. For example, a grid indicating the coordinate of the fixation is displayed on the fixation lamp position display region 513. For example, the position of the fixation is displayed as a light spot on the grid. Further, when an operation unit selects a point on the grid, the drive and control unit 114 changes the lighting position 265 of the fixation lamp 256 according to the selected position. Note that the coordinate indicating the current position of the fixation can be displayed as a numerical value on the fixation lamp position display region 513. In this case, changing the displayed numerical value can change the lighting position 265.

The Hartmann image detected by the wave-front sensor 255 is displayed on the wave-front display region 514 by the display control unit 112. Note that the wave-front display region 514 can constantly be provided, or can also be popped up as another window when the aberration measurement button 506 is selected, the measurement of the aberration is started and a Hartmann image is obtained. Configuring the wave-front display region 514 to pop up can efficiently use the screen of the liquid crystal monitor 105 while the aberration is not measured.

The WFSLO image generated by the image generation unit 111 is displayed on the WFSLO display region 515 by the display control unit 112.

The signal strength of the WFSLO image is displayed on the WFSLO strength display region 516 by the display control unit 112. More specifically, the signal strength of the WFSLO image is displayed as a time-series graph.

When the WFSLO recording button 517 is selected, the drive and control unit 114 records the WFSLO image, for example, in a storage unit 800 (not illustrated in the drawings) such as a Hard Disk Drive (HDD).

The aberration-corrected AOSLO image is displayed on the AOSLO display region 518 by the display control unit 112.

The signal strength of the AOSLO image is displayed on the AOSLO strength display region 519 by the display control unit 112. More specifically, the signal strength of the AOSLO image is displayed as a time-series graph.

When the AOSLO recording button 520 is selected, the drive and control unit 114 records the AOSLO image, for example, in a storage unit 800 (not illustrated in the drawings) such as a HDD.

When the autofocus button 521 is selected, the drive and control unit 114 automatically adjusts the positions of the lenses 235-10, 235-14, 235-16, and 235-18, such that the value of the defocus is reduced.

When the aberration correction button 522 is selected, the drive and control unit 114 automatically adjusts the spatial light modulator 259 in a direction in which the aberration is reduced.

In this case, when the aberration stored as the aberration of the eye (for example, the right eye) differing from the currently-imaged eye (for example, the left eye) and linked to the position of the fixation lamp is stored in the storage unit 800, the aberration of the left eye is adjusted in such a way as to approximate the corresponding aberration. This facilitates the comparison between the diagnoses because the AOSLO images of the left and the right eyes at the imaging positions corresponding to each other can be compared at the same aberration. Note that the fixation lamp positions of the left and the right eyes that correspond to each other are mirror-reversed positions on the display region of the fixation lamp.

The imaging condition setting button 523, for example, includes an imaging angle of view setting button, a frame rate setting button, and an imaging time setting button. For example, the imaging angle of view setting button includes a plurality of buttons corresponding to a plurality of angles of view, respectively, so that the examiner can take an image at a desired angle of view by selecting a button corresponding to the desired angle of view. The frame rate setting button, and the imaging time setting button is configured similarly to the imaging angle of view setting button.

The depth adjustment button 524, for example, is a slider and the drive and control unit 114 drives the lens 235-10 according to the travel distance and the travel direction of the slider. Note that the depth adjustment button 524 is not limited to a slider and anther configuration can be used as long as the configuration can drive the lens 235-10.

The aberration of the defocus element (μm unit) and the whole aberration (μm RMS unit) determined by the aberration determination unit 113 are displayed on an aberration display region 525 by the display control unit 112. Note that only one of the aberrations can be displayed. Note that the unit of the displayed aberration is not limited to the above-mentioned unit and another unit can be used.

Hereinafter, the description goes back to the flowchart illustrated in FIG. 6.

[Step S2]

Pressing the execute button 501 on the control software screen displays an image of the anterior eye portion on the anterior eye portion display region 512. When the center of the pupil is not correctly displayed on the center of the screen, the head portion 102 is moved to an approximately correct position using the joystick 107, first. When a further adjustment is required, the electric-powered stage travel button 503 on the control screen is pressed in order to slightly move the jaw receiver 108 by the drive and control unit 114.

[Step S22]

Subsequently, the drive and control unit 114 opens the shutter 291-2 for the WFSLO that has been closed. The state in which the shutter 291-2 for the WFSLO is opened is displayed on the shutter state display region 509. Further, the state in which the shutters 291-1 and 291-3 are closed is displayed on the shutter state display region 509.

Note that the timing of opening the shutter 291-2 for the WFSLO can be the time when the execute button 501 on the control software screen is selected, the time when the control software is started, or the time before the image of the anterior eye portion is displayed on the anterior eye portion display region 512.

[Step S3]

When the image of the anterior eye portion is displayed at an approximately correct position, a WFSLO image is displayed on the WFSLO display region 515. For example, the examiner sets the fixation lamp at the center position of the fixation lamp position display region 513 to induce the line of sight of the eye under examination 207 to the center. Note that the WFSLO measurement button 505 is automatically selected, for example, when the control software is started or when the execute button 501 is selected.

Next, the examiner adjusts the focus adjustment button 504 while watching the strength of the WFSLO image displayed on the WFSLO strength display region 516 in order to increase the WFSLO strength. At that time, the signal strength detected at a WFSLO portion is displayed in chronologic order on the WFSLO strength display region 516 as the time is shown on the horizontal axis and the signal strength is shown on the vertical axis. Note that adjusting the focus adjustment button 504 causes the positions of the lenses 235-10, 235-14, 235-16, and 235-18 to simultaneously be adjusted by the drive and control unit 114.

When the WFSLO image is photographically displayed, the examiner presses the WFSLO recording button 517 to store the WFSLO data (the WFSLO image).

[Step S4]

After checking the WFSLO image stored in step S3 and displayed on the WFSLO display region 515, the examiner determines the position where an AOSLO image is to be obtained using a way to be described below. Next, the examiner induces the line of sight of the eye under examination 207 such that the position is placed, for example, at the center of the WFSLO display region 515.

There are two ways to determine the position where the AOSLO image is to be obtained. One is the way in that the position of the fixation lamp is instructed at the fixation lamp position display region 513. The other is the way in that the desired position of the WFSLO image is clicked on the WFSLO display region 515. The pixels on the WFSLO display region 515 are linked to the position of the fixation lamp such that the drive and control unit 114 automatically moves the position of the fixation lamp according to the clicked position in order to induce the line of sight to the desired position. Note that it is not necessary to cause the light ejected from the light source 201-2 for obtaining the WFSLO image to enter the eye under examination 207 during step S4 because the line of sight of the eye under examination is induced using the WFSLO image stored in step S3.

After the fact that the position where the AOSLO image is to be obtained is moved to the center of the WFSLO display region 515 is confirmed, the process goes to the next procedure. Note that, in the present exemplary embodiment, the region where the AOSLO image is to be obtained is a rectangular region having a predetermined size and having the optical axis of the optical system illustrated in FIG. 2 as its center. In other words, the region where the AOSLO image is to be obtained is a rectangular region having a predetermined size and having the center of the WFSLO display region 515 as its center. Note that the region where the AOSLO image is to be obtained is not limited to the above and can arbitrarily be changed.

Further, the position of the fixation can be adjusted again after the WFSLO image is obtained again and it is confirmed whether the desired position of the eye under examination 207 is placed at the center of the WFSLO display region 515 after the position of the fixation lamp has been changed. In this case, when the incidence of the measurement light from the light source 201-3 into the eye under examination 207 is limited, the limitation is lifted in order to cause the measurement light to enter the eye under examination 207. This can surely move the desired position of the eye under examination 207 to the center of the WFSLO display region 515 and can shorten the period of time when the light irradiates the eye under examination 207.

[Step S44]

When the aberration measurement button 506 is selected, the drive and control unit 114 closes the shutter 291-2. Closing the shutter 291-2 limits (for example, blocks) the incidence of the light ejected from the light source 201-2 into the eye under examination 207. Storing the WFSLO image can trigger the drive and control unit 114 to close the shutter 291-2.

[Step S45]

Next, the drive and control unit 114 opens the shutter 291-3. Opening the shutter 291-3 causes the light ejected from the light source 201-3 to enter the eye under examination 207. Note that, for example, the fixation lamp 256 is lighted when the control software is started, or when the execute button 501 is selected. In other words, the drive and control unit 114 that is a control unit causes the first measurement light to enter the eye under examination while the light ejected from the fixation lamp enters the eye under examination.

Further, the fact that the shutter 291-3 is opened and the fact that the shutters 291-1 and 291-2 are closed are displayed on the shutter state display region 509.

[Steps S5 and S6]

Next, the display control unit 112 displays the Hartmann image detected at the wave-front sensor 255 on the wave-front display region 514. The display control unit 112 displays the aberration calculated according to the Hartman image on the aberration display region 511. The aberration is displayed while being divided into the defocus element (μm unit) and the whole aberration (μm RMS unit). At that time, the aberration can be measured in this step because the positions of the lenses 235-10 and 235-16 that are the focus lenses for the AOSLO measurement light and the beacon light are adjusted in step S3.

Pressing the autofocus button 521 at that time causes the drive and control unit 114 to automatically adjust the positions of the lenses 235-10, 235-14, 235-16, and 235-18 in order to reduce the value of the defocus.

Next, pressing the aberration correction button 522 causes the drive and control unit 114 to automatically adjust the spatial light modulator 259 in a direction in which the difference from the aberration of the other eye stored in the storage unit 800 and corresponding to the aberration of the eye under examination is reduced. Note that the display control unit 112 displays the value of the aberration on the liquid crystal monitor 105 in real time. At that time, the drive and control unit 114 compares the difference between the aberrations and the threshold determined in advance. When the difference between the aberrations becomes the threshold determined in advance or less, the drive and control unit 114 automatically presses the AOSLO measurement button 507 and the process goes to the next procedure. When the aberration becomes the threshold determined in advance (for example, 0.03 μm RMS) or less while the value of the corresponding aberration is not stored in the storage unit 800 at that time, the drive and control unit 114 automatically presses the AOSLO measurement button 507. Then, the aberration at that time is stored in the storage unit 800 while being linked to the position of the fixation lamp and the category of the imaged eye.

On the other hand, when the aberration does not become the threshold or less, the examiner can move the next procedure by pressing the AOSLO measurement button 507 after pressing the aberration correction suspending button 508 to suspend the aberration correction. Note that the threshold is not limited to the above-mentioned value and can be a given value. When the aberration calculated by the aberration determination unit 113 does not become the threshold or less for a predetermined period of time, the drive and control unit 114 can automatically select the AOSLO measurement button 507.

[Step S66]

When the difference between the aberrations or the aberration becomes the threshold determined in advance or less, the drive and control unit 114 closes the shutter 291-3. In other words, when the AOSLO measurement button 507 is selected, the drive and control unit 114 closes the shutter 291-3. Closing the shutter 291-3 limits (for example, blocks) the incidence of the light ejected from the light source 201-3 into the eye under examination 207.

[Step S67]

When the shutter 291-3 is closed, the drive and control unit 114 opens the shutter 291-1. In other words, when the AOSLO measurement button 507 is selected, the drive and control unit 114 opens the shutter 291-1. In other words, from the state in which the drive and control unit 114 causes the first measurement light to enter the eye under examination and limits the incidence of the second measurement light into the eye under examination, the drive and control unit 114 limits the incidence of the first measurement light into the eye under examination and then causes the second measurement light to enter the eye under examination, or opens the shutter 291-1. This causes the light ejected from the light source 201-1 to enter the eye under examination 207. The fact that the shutter 291-1 is opened and the fact that the shutters 291-2 and 291-3 are closed are displayed on the shutter state display region 509.

[Step S7]

The aberration-corrected AOSLO image is displayed on the AOSLO display region 518. Further, the signal strength of the AOSLO image is displayed in chronological order on the AOSLO strength display region 519, similarly to the WFSLO strength display region 516.

When the signal strength is insufficient, the examiner adjusts the focus and the jaw receiving position while watching the AOSLO strength display region 519 in order to increase the signal strength.

Further, the examiner can designate the imaging angle of view, the frame rate, and the imaging time with the imaging condition setting button 523.

Further, the examiner can adjust the imaging range in the depth direction of the eye under examination 207 by adjusting the depth adjustment button 524 and moving the lens 235-10. Specifically, adjusting the depth adjustment button 524 can obtain the image of a desired layer, for example, a neuroepithelial layer, a nerve fiber layer, or a pigmented layer.

When the AOSLO image is photographically displayed, the examiner presses the AOSLO recording button 520 to store the AOSLO data (the AOSLO image). After that, the drive and control unit 114 limits the incidence of the measurement light 206-1 into the eye under examination 207.

[Step S77]

When the AOSLO image is stored, the shutter 291-1 for the AOSLO is closed in order to limit the incidence of the measurement light 206-1 into the eye under examination. The fact that all of the shutters 291-1 to 291-3 are closed is displayed on the shutter state display region 509.

[Step S8]

The examiner determines whether to change the imaging position. When the examiner changes the imaging position, the process goes back to step S4. On the other hand, when the examiner does not change the imaging position, the process goes the next procedure. Note that an imaging position changing button can be displayed on the liquid crystal monitor 105 such that, when the imaging position changing button is selected, the control PC 106 can determine that the imaging position is changed. On the other hand, when the imaging position changing button is not selected during a predetermined period of time after the AOSLO image has been stored, the control PC 106 can determine that the imaging position is not changed.

[Step S9]

The examiner determines whether to switch the eye from the left eye to the right eye. In other words, after the photography of one eye (for example, the left eye) has been completed, the examiner switches the eye to the other eye (for example, the right eye). When the examiner switches the eye, the process goes back to step S2. This enables the control PC 106 to perform the process for causing the imaging light to irradiate an eye in the same order as the process for imaging the other eye. This prevents the last photography of one eye from wrongly being performed on the other eye. Further, the operator does not manually switch the order of photography. This can promote the efficiency of the process.

On the other hand, when the left and right eyes are not switched, the process goes to the next procedure. Note that a left and right eyes switching button can be displayed on the liquid crystal monitor 105 such that, when the left and right eyes switching button is selected, the control PC 106 can determine that the left eye is switched to the right eye. On the other hand, when the left and right eyes switching button is not selected during a predetermined period of time after the AOSLO image has been stored, the control PC 106 can determine that the left eye is not switched to the right eye. Note that the order of step S8 and step S9 can be reversed.

[Step S10]

The examiner presses the STOP button 502 to stop the control software. The control software is stopped and a sequence of the imaging operation is terminated.

[Check of the Image]

Figure 8:
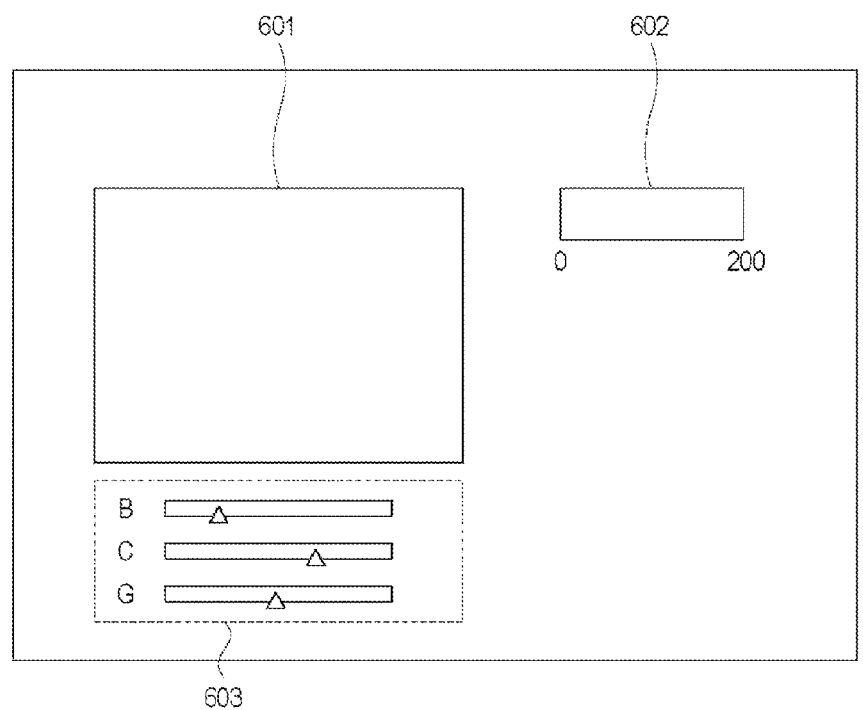
FIG. 8 is a view of an exemplary structure of the image viewer software in an AOSLO device according to an exemplary embodiment of the present invention.

Next, the method for imaging and checking the imaged data with the AOSLO device 101 in the present exemplary embodiment will be described using FIG. 8. FIG. 8 is a view of an exemplary configuration of the screen of the image viewer software in the present exemplary embodiment.

When the viewer software for visualizing the taken image data with the software control unit 110, a viewer software screen illustrated in FIG. 8 is displayed on the liquid crystal monitor 105 by the display control unit 112.

The viewer software can create an image by reading the stored WFSLO date or AOSLO date.

The viewer software screen includes an image display region 601, an image number selecting portion 602, and an image quality adjusting portion 603.

The image selected using the image number selecting portion 602, for example, an AOSLO image is displayed on the image display region 601. Alternatively, display switching means such as a tab can be provided such that a WFSLO image corresponding to the AOSLO image can be displayed on the image display region 601. This enables the comparison between the AOSLO image and the WFSLO image with ease. Alternatively, the AOSLO image and the WFSLO image can be displayed next to each other.

The image number selecting portion 602 is a unit for selecting a desired AOSLO image from among a plurality of AOSLO images obtained by the AOSLO device 101. For example, the image number selecting portion 602 is a slider. The position of the slider is linked to the image numbers of the AOSLO images so that the examiner can select a desired AOSLO image by moving the slider using an instruction unit. Although the number of shots is changed depending on the measuring time, the image numbers are put on the images in a chronological order. Note that the image number selecting portion 602 is not limited to the slider and can be a region where the image number can directly be input.

The image quality adjusting portion 603 is a slider for adjusting the brightness, the contrast, the gamma of an image (illustrated as "B", "C", and "G" in the drawing, respectively). Sliding the sliders from side to side can adjust the image quality. The control PC 106 adjusts the image quality of an image such as an AOSLO image based on the input to the image quality adjusting portion 603.

Further, the viewer software screen is not limited to the above-mentioned example and, for example, the position of the fixation at the time when the AOSLO image displayed on the image display region 601 has been obtained can be displayed as a coordinate value or a figure. Alternatively, the coordinate of the face receiving portion 104 at the time when the AOSLO image displayed on the image display region 601 has been obtained can be displayed. Further, the luminance or amplitude of the AOSLO image with respect to the scanning time at the time when the AOSLO image displayed on the image display region 601 has been obtained can be displayed as a graph. Further, the information indicating at least one of the lens positions of the lenses 235-10, 235-14, 235-16, and 235-18 at the time when the AOSLO image displayed on the image display region 601 has been obtained can be displayed.

Note that the AOSLO image can be displayed as a moving image on the image display region 601. In such a case, as for the parameter, for example, of the position of the fixation at the time when the AOSLO image has been obtained, the values of the parameter corresponding to the AOSLO image are sequentially displayed.

As described above, according to the present exemplary embodiment, an AOSLO image can be obtained as lights from a plurality of light sources are prevented from simultaneously entering an eye under examination. Thus, the reduction in the image quality can be prevented as the safety is ensured.

Further, the fixation lamp 256 is lighted while the light ejected from the light source 201-3 enters the eye under examination 207. Thus, the movement of the eye under examination 207 can be suppressed and the aberration can accurately be measured.

Further, the incidence of the measurement light ejected from the light source 201-2 into the eye under examination 207 is limited and the position where an AOSLO image is to be obtained is adjusted using a WFSLO image after the WFSLO image has been stored. This can further reduce the light quantity irradiating the subject.

Further, according to the present exemplary embodiment, the time to stably eject a light after the light sources 201-1 to 201-3 have been turned off is not required when the limitation of the incidence of the measurement light into under examination 207 is lifted. Thus, the reduction in the image quality can be prevented as the safety is ensured, and the examination time can be prevented from being long.

Further, the states of opening and closing of the shutters 291-1 to 291-3 are displayed on the shutter state display region 509, so that the examiner can clearly and easily get which measurement light 206-1, 206-2, or 206-3 irradiates the eye under examination 207. This improves the certainty of the imaging operation.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An ophthalmic device, comprising:
   a measurement optical system configured to measure an aberration of an eye to be examined by using a return light from the eye which a first measurement light emitted from a first light source enters;
   a first imaging optical system configured to capture a first fundus image by using a first return light from the eye which a second measurement light emitted from a second light source enters, the first return light being corrected by a correction unit based on the aberration;
   a second imaging optical system configured to capture a second fundus image by using a second return light from the eye which a third measurement light emitted from a third light source enters, the second fundus image being larger than the first fundus image; and
   a control unit configured to cause the measurement lights to enter the eye in an order of the measurement lights from the third light source, the first light source, the second light source when an eye for imaging object is switched from a first eye of the both eyes to a second eye of the both eyes, and to enter the eye in an order of the measurement lights from the first light source, the second light source when an imaging position in the eye is changed.

2. The ophthalmic device according to claim 1, further comprising:
   a first shutter placed at the measurement optical system;
   a second shutter placed at the first imaging optical system; and
   a third shutter placed at the second imaging optical system, wherein the control unit opens the shutters in an order of the third shutter, the first shutter, and the second shutter or in an order of the first shutter and the second shutter.

3. The ophthalmic device according to claim 1, further comprising:
   a display control unit configured to display a display form showing incidence of the first measurement light and the second measurement light into the eye on a display unit.

4. The ophthalmic device according to claim 2, further comprising:
   a display control unit configured to display a display form showing states of opening and closing of the shutters on a display unit.

5. The ophthalmic device according to claim 1, wherein the control unit closes all of the shutters at the time when the eye for imaging object is switched from the first eye to the second eye.

6. The ophthalmic device according to claim 1, further comprising;
   a first detector configured to convert the first return light into a first signal;
   a second detector configured to convert the second return light into a second signal; and
   a generation unit configured to generate first and second planar images of the eye using each of the first signal and the second signal.

7. The ophthalmic device according to claim 1, wherein the correction unit includes a spatial light modulator.

8. The ophthalmic device according to claim 1, further comprising:
   a head unit configured to include the measurement optical system, the first imaging optical system and the second imaging optical system; and
   a stage unit configured to move the head unit in a horizontal direction when the eye for imaging object is switched from the first eye to the second eye.

9. A control method for controlling an ophthalmic device comprising a first light source configured to emit a first measurement light, a second light source configured to emit a second measurement light and a third light source configured to emit a third measurement light, the method comprising:
   capturing a first fundus image by using a return light from an eye to be examined which the third measurement light enters;
   measuring an aberration in a return light from the eye which the first measurement light enters;
   correcting the aberration in the return light;
   capturing a second fundus image by using a return light from the eye which the second measurement light enters, the second fundus image being smaller than the first fundus image;
   determining whether an imaging position in the eye is changed and whether an eye for imaging target is switched from a first eye of a both eyes to a second eye of the both eyes; and
   repeating the steps of capturing the first fundus image, measuring the aberration, correcting the aberration and capturing a second fundus image when the eye for imaging object is switched from the first eye to the second eye, and repeating the steps of measuring the aberration, correcting the aberration and capturing a second fundus image when the imaging position in the eye is changed.

10. A non-transitory computer-readable storage medium storing computer-executable instructions for causing a computer to execute the method according to claim 9.

* * * * *